United States Patent [19]
Ziegler et al.

[11] Patent Number: 6,130,246
[45] Date of Patent: Oct. 10, 2000

[54] PESTICIDES

[75] Inventors: Hugo Ziegler, Witterswil; René Zurflüh, Basel, both of Switzerland

[73] Assignee: Novartis Crop. Protection Inc., Greensboro, N.C.

[21] Appl. No.: 08/999,934

[22] Filed: Sep. 19, 1997

[30] Foreign Application Priority Data

Sep. 27, 1996 [CH] Switzerland .............................. 2375/96
Nov. 1, 1996 [CH] Switzerland .............................. 2708/96

[51] Int. Cl.$^7$ ........................................ A01N 37/52
[52] U.S. Cl. .............................. 514/508; 560/19; 560/21; 560/22; 560/23; 560/168; 564/253; 564/265; 568/337
[58] Field of Search .................. 560/19, 21, 22, 560/23, 168; 514/508; 568/337; 564/253, 265

[56] References Cited

U.S. PATENT DOCUMENTS

| | | | |
|---|---|---|---|
| 4,705,896 | 11/1987 | Van Der Puy et al. ................. | 564/265 |
| 5,105,021 | 4/1992 | Akieda et al. ........................... | 568/337 |
| 5,238,956 | 8/1993 | Clough et al. ........................... | 514/506 |

*Primary Examiner*—Gary Geist
*Assistant Examiner*—Taylor Victor Oh
*Attorney, Agent, or Firm*—Michael P. Morris

[57] ABSTRACT

The compounds of formula I

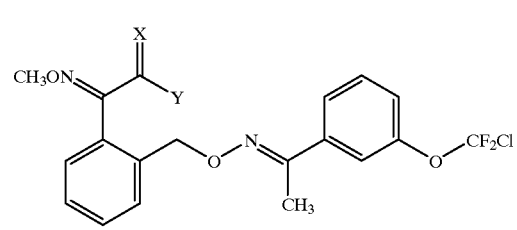

wherein:

a) X is O, and
  Y is OC$_1$–C$_4$alkyl; or
b) X is O or S, and
  Y is NHCH$_3$ have fungicidal properties and can be used in plant protection for controlling and preventing disease infestation.

10 Claims, No Drawings

PESTICIDES

The invention relates to novel pesticidally active compounds of formula I

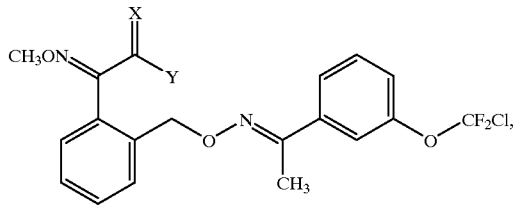

wherein:
a) X is O, and
  Y is OC$_1$–C$_4$alkyl; or
b) X is O or S, and
  Y is NHCH$_3$.

The compounds of formula I and their fungicidal activity have been described generically, but not as individual compounds, in EP-A-460 575, EP-A463 488 and WO E)4/26700.

It has been found that the compounds according to the invention are distinguished by having an extraordinarily good fungicidal activity, especially in cereals. Preference is given to compounds wherein a) X is O
  Y is OCH$_3$ or OC$_2$H$_5$, especially OCH$_3$, and those wherein
b) X is O or S, and
  Y is NHCH$_3$.

C$_1$–C$_4$alkyl is methyl, ethyl, n-propyl, iso-propyl, n-butyl, sec-butyl, iso-butyl or tert-butyl.

The compounds of formula I can be prepared by known methods in accordance with the Reaction Scheme, as follows:

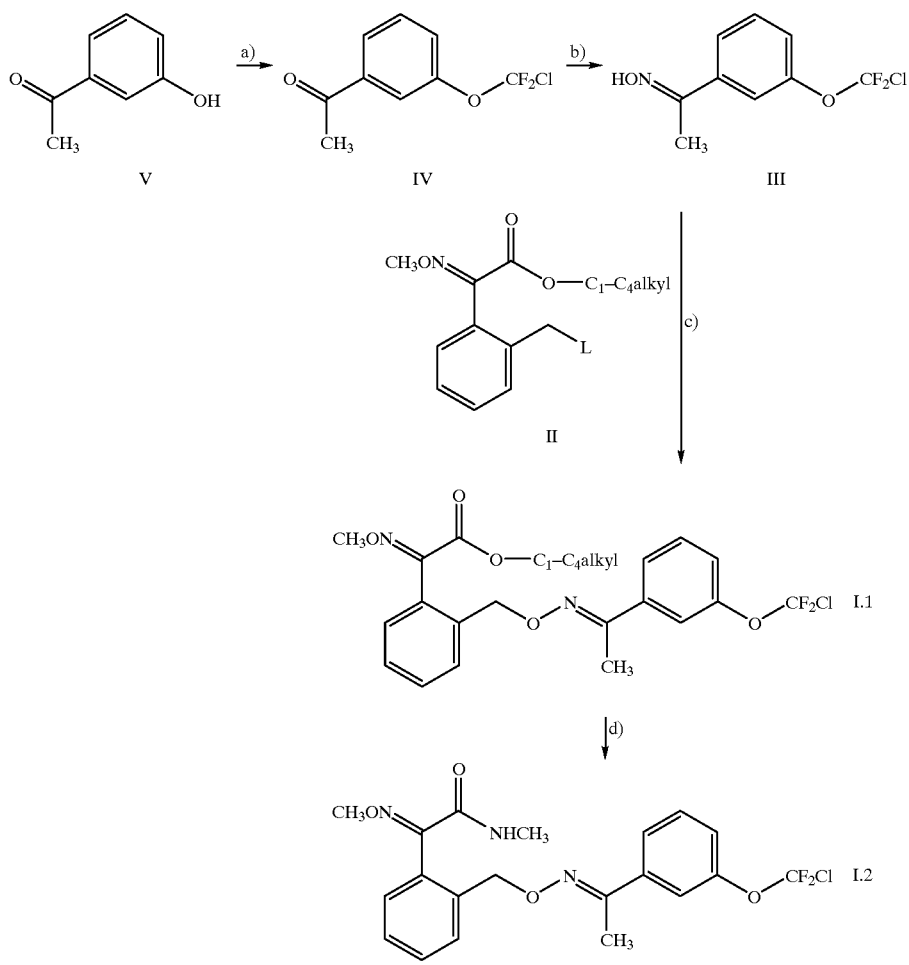

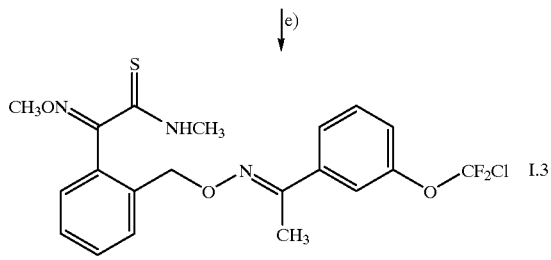

Reaction with a) phosgene or diphosgene or CCl$_4$ in HF;

b) hydroxylamine or its salt;

c) a compound of formula II wherein L is a leaving group, preferably a halide, especially the chloride and the bromide, under basic conditions;

d) methylamine;

e) a thionating agent, preferably phosphorus pentasulfide or 4-methoxyphenylthiophosphoric acid cyclodithioanhydride ("Lawesson's reagent").

The reactants can be reacted with one another as such, that is to say vithout the addition of a solvent or diluent, for example in the melt. Usually, however, the addition of an inert solvent or diluent or a mixture thereof is advantageous. There may be mentioned as examples of such solvents and diluents: aromatic, aliphatic and alicyclic hydrocarbons and halogenated hydrocarbons, such as benzene, toluene, xylene, chlorobenzene, bromobenzene, petroleum ether, hexane, cyclohexane, dichloromethane, trichiloromethane, dichloroethane or trichloroethane; ethers, such as diethyl ether, tert-butyl methyl ether, tetrahydrofuran or dioxane; ketones, such as acetone or methyl ethyl ketone; alcohols, such as methanol, ethanol, propanol, butanol, ethylene glycol or glycerol; esters, such as ethyl acetate or butyl acetate; amides, such as N,N-dimethylformamide, N,N-dimethylacetamide, N-methylpyrrolidone or hexamethylphosphoric acid triamide; nitriles, such as acetonitrile; and sulfoxides, such as dimethyl sulfoxide. Bases used in excess, such as triethylamine, pyridine, N-methylmorpholine or N,N-diethylaniline, may also serve as solvents or diluents.

The reaction can also be carried out with phase transfer catalysis in an organic solvent. for example methylene chloride or toluene, in the presence of an aqueous basic solution, for example sodium hydroxide solution, and of a phase transfer catalyst, foi example tetrabutylammonium hydrogen sulfate.

The invention relates also to the novel intermediates of formulae IV and III.

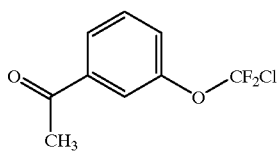

IV

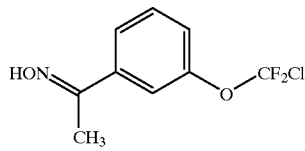

III

The compounds of formula I can be used in the agricultural sector and related fields preventively and/or curatively as active ingredients in the control of plant diseases. The compounds of formula I according to the invention are distinguished by having good activity even at low rates of concentration, by being well tolerated by plants and by being environmentally friendly. They possess very advantageous, especially systemic, properties and can be used for the protection of a large number of cultivated plants. With the compounds of formula I it is possible to inhibit or destroy the pests that occur on plants or on parts of plants (the fruit, blossom, leaves, stems, tubers or roots) of various crops of useful plants, while parts of plants that grow later are also protected, for example against pilytopathogenic microorganisms.

The compounds I can also be used as dressings in the treatment of seed (fruit, tubers, grains) and plant cuttings to provide protection against fungus infections, as well as against phytopathogenic fungi that occur in the soil.

The compounds I are effective, for example, against phytopathogenic fungi belonging to the following classes: Fungi imperfect (e.g. Botrytis, Pyricularia, Helminthosporium, Fusarium, Septoria, Cercospora und Alternaria); Basidiomycetes (e.g. Rhizoctonia, Hemileia, Puccinia); Ascomycetes (e.g. Venturia and Erysiphe, Podosphaera, Monilinia, Uncinula) and Oomycetes (e.g. Phytophthora, Pythium, Plasmopara).

Within the scope of the invention, target crops for plant protection use include, for example, the following species of plants: cereals (wheat, barley, rye, oats, rice, maize, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); and plants such as tobacco, nuts, coffee, aubergines, sugar cane, tea, pepper, vines, hops, bananas and natural rubber plants, as well as ornamentals.

The compounds I are usually used in the form of compositions and can be applied to the area or plant to be treated simultaneously or in succession with further active ingredients.

These further active ingredients may be, for example, fertilizers, microriutrient donors or other preparations that influence plant growth. It is also possible to use selective herbicides, and insecticides, fungicides, bactericides, nematicides, molluscicides or mixtures of several of these preparations, if desired together with further carriers, surfactants or other application-promoting adjuvants customarily employed in formulation technology.

The compounds of formula I can be mixed with other fungicides, producing in some cases unexpected synergistic effects.

Especially preferred mixing partners are azoles, such as propiconazole difenoconazole, cyproconazole, epoxiconazole, tebuconazole, tetraconazole, fenbuconazole, metconazole, bromuconazole;

also fenpropidine, fenpropimorph, cyprodinil, pyrimethanil, benzo-1,2,3-thiadiazole-7-carbothioic acid S-methyl ester;

strobilurins, such as azoxystrobin and cresoxime methyl.

Suitable carriers and adjuvants may be solid or liquid and are the substances usefully employed in formulation technology, for example natural or regenerated mineral substances, solvents, dispersants, wetting agents, tackifiers, thickeners, binders or fertilizers.

A preferred method of applying a compound of formula I, or an agrochenical composition comprising at least one of those compounds, is application to the foliage of the plants (foliar application). The frequency and the rate of application depend upon the risk of infestation by the pathogen in question. However, the compounds of formula I can also penetrate the plants through the roots via the soil (systemic action) if the locus of the plants is impregnated with a liquid formulation or if the active ingredients are incorporated into the soil in solid form, e.g. in granular form (soil application). In the case of paddy rice crops, such granules may be applied in metered amounts to the flooded rice field. The compounds of formula I may, however, for seed treatment, also be applied to the seed grains (coating), either by impregnating the seeds or tubers with a liquid formulation of the active ingredient or by coating them with a solid formulation.

The compounds of formula I are used in unmodified form or, preferably, together with the adjuvants conventionally employed in formulation technology. For that purpose they are advantageously formulated in known manner e.g. into emulsifiable concentrates, coatable pastes, directly sprayable or dilutable solutions, dilute emulsions, wettable powders, soluble powders, dusts or granules, for example by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are generally from 1 g to 2 kg of active ingredient (a.i.) per hectare (ha), preferably from 10 g to 1 kg a.i./ha, especially from 20 g to 600 g a.i./ha. When used as seed dressings, rates of from 10 mg to 1 g of active ingredient per kg of seed are advantageously used.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredient with extenders, such as solvents, solid carriers and, where appropriate, surface-active compounds (surfactants).

Suitable solvents are: aromatic hydrocarbons, preferably the fractions containing 8 to 12 carbon atoms, such as xylene mixtures or substituted naphthalenes, phthalates, such as dibutyl phthalate or dioctyl phthalate, aliphatic hydrocarbons, such as cyclohexane, or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; and water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent cariiers are, for example, calcite or sand. In addition, a great number of pregranulated materials of inorganic or organic nature can be used, such as dolomite or pulverised plant residues.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Examples of non-ionic surfactants to be mentioned are nonylphenol polyethoxyethanols, castor oil polyglycol ethers, polypropylene/polyethylene oxide adducts, tiibutylphenoxypolyethoxyethanol, polyethylene glycol and octylphenoxypolyethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent(s), at least one $C_8$–$C_{22}$alkyl radical and, as further substituents, unsubstituted or halogenated lower alkyl, benzyl or hydroxy-lower alkyl radicals.

Other surfactants customarily employed in formulation technology are krown to one skilled in the art or can be found in the relevant specialist literature.

The agrochemical compositions normally comprise 0.1 to 99% by weight, especially 0.1 to 95% by weight. compound of formula I, 99.9 to 1% by weight, especially 99.8 to 5% by weight, of a solid or liquid adjuvant, and 0 to 25% by weight, especially 0.1 to 25% by weight, of a surfactant.

Whereas commercial products will preferably be formulated as concentraites, the end user will normally employ dilute formulations.

The compositions may also comprise further adjuvants, such as stabilizers, antifoams, viscosity regulators, binders or tackifiers, as well as fertilizers or other active ingredients for obtaining special effects.

1. PREPARATION EXAMPLES

Temperatures are given in degrees Celsius.

Example P-1

Preparation of 1-(3-(chloro-difluoro-methoxy)-phenyl)-ethanone (IV)

25 g of 3-hydroxyacetophenone are placed in an autoclave. After coolingj by means of a dry-ice bath, 94 g of HF are applied under pressure. Then, at room temperature, 75 g of diphosgene are applied under pressure. After 6 days, HF is removed by suction and the residue is flushed into ice-water using ethyl acetate. The mixture is rendered neutral with $NH_3$ solution. The organic phase is washed twice with saturated NaCI solution and the washing liquors are back-extracted with ethyl acetate. The combined organic phases are dried over sodium sulfate. Filtration and concentration by evaporation using a rotary evaporator yield a reddish yellow oil. After chromatography on silica gel to remove the starting material) using hexane/diethyl ether 1:1, 23.5 g of desired product are obtained in the form of a yellow oil.

B.p. 105° C./10 mm.

Example P-2

Preparation of 1 -(3-(chloro-difluoro-methoxy)-phenyl)-ethanone oxime (III)

A mixture of 3.3 g of 1-(3-(chloro-difluoro-methoxy)-phenyl)-ethanone, 1.4 g of hydroxylamine hydrochloride and 10 ml of pyridine is stirred at 50° C. for 2 hours. It is then poured into ice-water, extracted with diethyl ether and concentrated using a rotary evaporator, and any pyridine still present is removed azeotropically by means of toluene. Drying under reduced pressure at 60° C. yields 3.75 g of the desired oxime in the form of an oil.

Example P-3

Preparation of 2-(1-(3-(chloro-difluoro-methoxy)-phenyl)-ethylideneaminoxymethyl)-phenyl)-methoximino-acetic acid methyl ester (I.1)

0.2 g of a 60% sodium hydride dispersion in mineral oil is washed with hexane, and 5 ml of N,N-dimethylformamide are added thereto. To that suspension there are) added 1.43 9 of 2-(bromomethylphenyl)glyoxylic acid methyl ester O-methyl oxime and 1.18 g of 1-(3-(chlorodifluoro-methoxy)-phenyl)-ethanone oxime. The reaction mixture is heated to 50° C. and stirred at room temperature for one hour. Ice-water is then added and extraction is carried out twice with 50 ml of ethyl acetate each time. The combined organic extracts are washed with water and dried over sodium sulfate and the solvent is distilled off under reduced pressure. The residue is purified by chromatography on silica gel using ethyl acetate/hexane (1:5% by volume to 1:4% by volume). 1.3 g of the desired product are obtained in the form of a colourless oil.

Example P-4

Preparation of 2-(2-(1-(3-(chloro-difluoro-methoxy)-phenyl)-ethylideneaminoxymethyl)-phenyl)-methoximino-N-methyl-acetamide (I.2)

6.6 g of the compound obtained in P-3 are stirred in 15 ml of a 33% ethanolic methylamine solution for 1 hour at room temperature. Ethanol and excess methylamirie are distilled off and the residue is filtered over silica gel using diethyl ether. The product is obtained in the form of an oil.

Example P-5

Preparation of 2-(2-(1-(3-(chloro-difluoro-methoxy)-phenyl)-ethylideneaminoxymethyl)-phenyl)-methoximino-N-methyl-thioacetamide (I.3)

2.2 g of the compound obtained in P-4 are dissolved in 20 ml of toluene, and 1.11 g of Lawesson's reagent are added thereto with stirring. The mixture is then s;tirred at 100–105° C. for 2 hours. It is then concentrated using a rotary evaporator and chromatographed on silica gel using hexane/diethyl ether 1:1. 1.72 9 of the desired thioamide are obtained in the form of an oil that crystallizes. M.p. 86–88° C.

2. FORMULATION EXAMPLES FOR ACTIVE INGREDIENTS (THROUGHOUT, PERCENTAGES, ARE BY WEIGHT)

| 2.1 Wettable powders | a) | b) | c) |
| --- | --- | --- | --- |
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is mixed with the adjuvants and the mixture is homogeneously ground in a suitable mill, affording wettable powders which can be diluted with Dater to give suspensions of any desired concentration.

| 2.2 Emulsifiable concentrate | |
| --- | --- |
| active ingredient | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution can be obtained from this concentrate by dilution with water.

| 2.3 Dusts | a) | b) |
| --- | --- | --- |
| active ingredient | 5% | 8% |
| talcum | 95% | — |
| kaolin | — | 92% |

Ready-for-use dusts are obtained by mixing the active ingredient with the carriers and grinding the mixture in a suitable mill.

| 2.4 Extruder granules | |
| --- | --- |
| active ingredient | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.5 Coated granules | |
| --- | --- |
| active ingredient | 3% |
| polyethylene glycol (mol. wt. 200) | 3% |
| kaolin | 94% |

The finely ground active ingredient is uniformly applied, in a mixer, to the, kaolin moistened with polyethylene glycol. Non-dusty coated granules are obtained in this manner.

| 2.6 Suspension concentrate | |
|---|---|
| active ingredient | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% emulsion in water | 0.8% |
| water | 32% |

The finely ground active ingredient is intimately mixed with the adjuvants, giving a suspension concentrate from which suspensions of any desired dilution can be obtained by dilution with water.

3. BIOLOGICAL EXAMPLES

Example B-1

Action against Puccinia Graminis on Wheat a) Residual-Protective Action 6 days after sowing, wheat plants are sprayed to drip point with an aqueous spray mixture (0.02% active ingredient), prepared from a wettable powder formulation of the active ingredient, and infected 24 hours later with a uredospore suspension of the fungus. After an incubation period of 48 hours (conditions: 95–100% relative humidity at 20°), the plants are placed in a greenhouse at 22°. Fungus infestation is evaluated 12 days after infection.

b) Systemic Action 5 days after sowing, wheat plants are watered with an aqueous spray mixture (0.006% active ingredient, based on the volume of the soil), prepared from a wettable powder formulation of the active ingredient. Care is taken that the spray mixture does not come into contact with parts of the plants that are above the soil. The plants are infected 48 hours later with a uredospore suspension of the fungus. After an incubation period of 48 hours (conditions 95–100% relative humidity at 20°), the plants are placed in a greenhouse at 22°. Fungus infestation is evaluated 12 days after infection.

The compounds exhibit good activity.

Example B-2

Action Against Phytophthora Infestans on Tomatoes a) Residual-Protective Action

After a cultivation period of three weeks, tomato plants are sprayed to drip point with an aqueous spray mixture (0.02% active ingredient), prepared from a wettable powder formulation of the active ingredient, and infected 24 hours later with a sporangia suspension of the fungus. Fungus infestation is evaluated 5 days after infection, a relative humidity of 90 to 100% and a temperature of 20° having been maintained during that period.

b) Systemic Action

After a cultivation period of three weeks, tomato plants are watered with an aqueous spray mixture (0.006% active ingredient, based on the volume of the soil) prepared from a wettable powder formulation of the active ingredient. Care is taken that the spray mixture does not come into contact with parts of the plants that are above the soil. After 48 hours, the plants are infected with a sporangia suspension of the fungus. Fungus infestation is evaluated 5 days after infection, a relative humidity of 90 to 100% and a temperature of 20° having been maintained during that period.

The compounds exhibit good activity.

Example B-3

Residual-Protective Action Against Cercospora Arachidicola on Groundnuts

Groundnut plants 10–15 cm in height are sprayed to drip point with an aqueous spray mixture (0.02% active ingredient), prepared from a wettable powder foriulation of the active ingredient, and infected 48 hours later with a conidia suspension of the fungus. The plants are incubated for 72 hours at 21° and high humidity and then placed in a greenhouse until the typical leaf specks appear. Evaluation of the action of the active ingredient is made 12 days after infection and is based on the number and size of the leaf specks.

The compounds exhibit good activity.

Example B-4

Action Against Plasmopara Viticola on Vines

Vine seedlings at the 4- to 5-leaf stage are sprayed to drip point with an aqueous spray mixture (0.02% active ingredient), prepared from a wettable powder forriulation of the active ingredient, and infected 24 hours later with a sporangia suspension of this fungus. Fungus infestation is evaluated 6 days after infection, a relative humidity of 95 to 100% and a temperature of 20° having been maintained during that period.

The compounds exhibit good activity.

Example B-5

Action Against Colletotrichum Lagenarium on Cucumbers

After a cultivation period of 2 weeks, cucumber plants are sprayed with a spray mixture (concentration 0.002%) prepared from a wettable powder formulation of the active ingredient. After 2 days, the plants are infected with a spore suspension ($1.5 \times 10^5$ spores/ml) of the fungus and incubated for 36 hours at 23° C. and high humidity. Incubation is then continued at normal humidity and about 22° C. The fungus infestation that has occurred is evaluated 8 days after infection.

The compounds exhibit good activity.

Example B-6

Residual-Protective Action Against Venturia Inaequalis on Apples

Apple cuttings with 10–20 cm long fresh shoots are sprayed to drip point with an aqueous spray mixture (0.02% active ingredient), prepared from a wettable powder formulation of the active ingredient, and infected 24 hours later with a conidia suspension of the fungus. The plants are incubated for 5 days at 90–100% relative humidity and placed in a greenhouse for a further 10 days at 20–24°. Fungus infestation is evaluated 12 days after infection.

The compounds exhibit good activity.

Example B-7

Action Against Erysiphe Graminis on Barley a) Residual-Protective Action

Barley plants about 8 cm in height are sprayed to drip point with an aqueous spray mixture (0.02% active ingredient), prepared from a wettable powder formulation of the active ingredient, and dusted 3 to 4 hours later with conidia of the fungus. The infected plants are placed in a greenhouse at 22°. Fungus infestation is evaluated 12 days after infection.

The compounds exhibit good activity.

b) Systemic Action

Barley plants about 8 cm in height are watered with an aqueous spray mixture (0.002% active ingredient, based on the volume of the soil) prepared from a wettable powder formulation of the active ingredient. Care is taken that the spray mixture does not come into contact with parts of the plants that are above the soil. The plants are dusted 48 hours later with conidia of the fungus. The infected plants are placed in a greenhouse at 22°. Fungus infestation is evaluated 12 days after infection.

The compounds exhibit good activity.

Example B-8

Action Against Podosphaera Leucotricha on Apple Shoots

Apple cuttings with approximately 15 cm long fresh shoots are sprayed with a spray mixture (0.06% active ingredient). The treated plants are infected 24 hours later with a conidia suspension of the fungus and placed in a controlled environment chamber at 70% relative humidity and 20° C. Fungus infestation is evaluated 12 days after infection.

The compounds exhibit good activity.

What is claimed is:

1. A compound of formula I

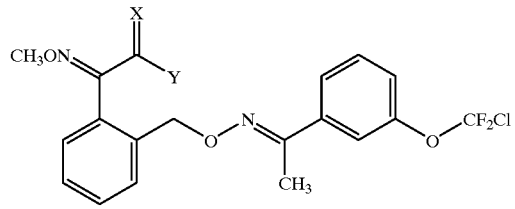

wherein:

X is O or S, and

Y is NHCH$_3$.

2. The compound according to claim 1, wherein:

X is O, and

Y is NHCH$_3$.

3. A compound of formula IV or III.

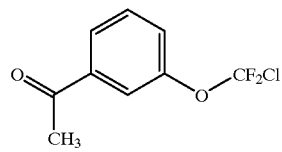

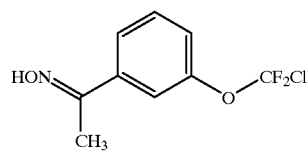

4. A composition for the protection of plants, parts of a plant or seeds against fungus infestation, which comprises a fungicidally effective amount of the compound according to claim 1 in free form or in agrochemically usable salt form, together with a carrier.

5. A composition according to claim 4 which comprises at least one further component having fungicidal activity.

6. A method of protecting plants, parts of a plant or seeds against fungus infestation, which comprises applying a fungicidally effective amount of the compound of formula I according to claim 1 to the plants, to parts of the plant or to the seeds and/or to the locus of the plants, or seeds.

7. The composition according to claim 4 in liquid or granular form.

8. The composition according to claim 5 wherein the at least one further component comprises an azole.

9. The method according to claim 6 wherein the compound is applied to the foliage of the plant.

10. Seed coated with the compound according to claim 1.

* * * * *